United States Patent [19]

Fobare et al.

[11] Patent Number: 4,792,614

[45] Date of Patent: Dec. 20, 1988

[54] SUBSTITUTED FURANS AS INHIBITORS OF 3-HYDROXY-3-METHYLGLUTARYL-CoA REDUCTASE

[75] Inventors: William F. Fobare, Newtown Square; Donald P. Strike, St. Davids, both of Pa.

[73] Assignee: American Home Products Corporation, New York, N.Y.

[21] Appl. No.: 82,013

[22] Filed: Aug. 5, 1987

[51] Int. Cl.$^4$ .................. C07D 309/30; C07D 307/34
[52] U.S. Cl. .................................. 549/292; 549/472; 549/496; 549/501
[58] Field of Search ............... 549/292, 472, 496, 501; 514/460, 461, 824, 471

[56] References Cited

U.S. PATENT DOCUMENTS

| | | | |
|---|---|---|---|
| 4,375,475 | 3/1983 | Willard et al. | 549/292 |
| 4,571,428 | 2/1986 | Kapa | 556/437 |
| 4,613,610 | 9/1986 | Wareing | 514/406 |
| 4,654,363 | 3/1987 | Prugh | 549/292 |

FOREIGN PATENT DOCUMENTS 8500653 6/1986 PCT Int'l Appl. .
2162179 1/1986 United Kingdom .

OTHER PUBLICATIONS

Hoffman et al., "3-Hydroxy-3-Methylglutaryl, etc" *J. Med Chem,* 29 159 (1986).
Derwent 84–201398/32 (Abstract of WO 8402-903.
Rosen et al., J. Am. Chem. Soc. 107, 3731 (1985).
Sletzinger et al., Tetrahedron Letters 26, 2951 (1985).
Stokker et al., J. Med. Chem. 28, 347 (1985).
Stokker et al., J. Med. Chem. 29, 170 (1986).

*Primary Examiner*—Glennon H. Hollrah
*Assistant Examiner*—Patricia L. Morris
*Attorney, Agent, or Firm*—Richard K. Jackson

[57] ABSTRACT

Compounds of the formula:

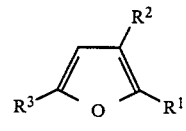

in which $R^1$ is —CH=CHCHCH$_2$CHCH$_2$CO$_2$M or
                         |        |
                        OH  OH

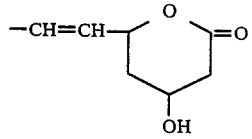

where M is hydrogen or alkyl; one of $R^2$ and $R^3$ is phenyl or substituted phenyl where the substituent is alkyl, alkoxy, halogen, trifluoromethyl, nitro, amino, cyano or carboxyl; and the other of $R^2$ and $R^3$ is hydrogen, alkyl, or a halogen; or a pharmaceutically acceptable salt thereof, are HMG—CoA reductase inhibitors useful in the treatment of atherosclerosis, hypercholesterolaemia, hyperlipaemia and similar disease states characterized by elevated cholesterol levels in the blood.

10 Claims, No Drawings

SUBSTITUTED FURANS AS INHIBITORS OF 3-HYDROXY-3-METHYLGLUTARYL-COA REDUCTASE

BACKGROUND OF THE INVENTION

With the discovery that the biosynthesis of cholesterol can be inhibited by compactin, and more effectively by mevinolin, considerable effort has been made in the attempt to obtain 3-hydroxy-3-methylglutaryl-coenzyme A reductase (HMG-CoA reductase) inhibitors of less complex structure, with limited success.

DESCRIPTION OF THE INVENTION

In accordance with this invention, there is provided a group of furan derivatives which possess HMG-CoA reductase inhibitory properties useful as antihypercholesterolemic agents in the treatment of disease states such as atherosclerosis, familial hypercholesterolaemia (homozygotes and heterozygotes), hyperlipaemia, and the like. The furan derivatives of this invention possess the following structural features:

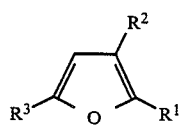

in which $R^1$ is —CH=CHCH(OH)CH$_2$CH(OH)CH$_2$CO$_2$M or

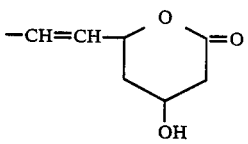

where

M is hydrogen or alkyl of 1 to 4 carbon atoms;
one of $R^2$ and $R^3$ is phenyl or substituted phenyl containing 1 or 2 substituents which are, independently, alkyl of 1 to 8 carbon atoms, alkoxy of 1 to 8 carbon atoms, halogen, trifluoromethyl, nitro, amino, cyano or carboxyl; and the other of $R^2$ and $R^3$ is hydrogen, alkyl of 1 to 8 carbon atoms, or a halogen;
or a pharmaceutically acceptable salt thereof.

The preferred compounds of this invention from the standpoint of production economics and availability of starting materials, are those of the formula:

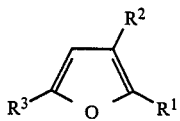

in which $R^1$ is —CH=CHCH(OH)CH$_2$CH(OH)CH$_2$CO$_2$M or

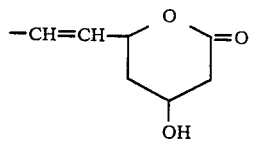

where

M is hydrogen or alkyl of 1 to 4 carbon atoms;
one of $R^2$ and $R^3$ is phenyl or substituted phenyl containing 1 or 2 substituents which are, independently, halogen, nitro or trifluoromethyl, and the other of $R^2$ and $R^3$ is hydrogen or alkyl or 1 to 4 carbon atoms;
or a pharmaceutically acceptable salt thereof.

In the above-described group of compounds, the halogen substituent may be chlorine, bromine, iodine or fluorine; the alkyl and alkoxy groups may be straight or branched chain, and the pharmaceutically acceptable salts are those derived conventionally from inorganic or organic bases which will neutralize the carboxylic acid where M is hydrogen, to supply the alkali metal (sodium or potassium), alkaline earth metal (calcium or magnesium), ammonium or amine (methylamine, ethylamine, propylamine, isoproplyamine, dimethylamine, diethylamine, di(hydroxyethyl)amine, and the like) cations. In the event that the substituted phenyl group representing $R^2$ or $R^3$ contains a carboxyl substituent, dibasic salts may be prepared. Similarly, those compounds containing an amino group on the substituted phenyl substituent representing $R^2$ or $R^3$ will form pharmaceutically acceptable acid addition salts with such acids as hydrochloric, hydrobromic, sulfuric, phosphoric, methane sulfonic, nitric, p-toluenesulfonic, acetic, citric, maleic, succinic acid, and the like.

The lactone (4-hydroxy-2H-pyran-2-one) group may be hydrolyzed or enzymatically opened in situ to afford the dihydroxyheptenoic acid group as a functional species which is usually the more potent form of the compound, at least in in vitro studies. The trans configuration of the tetrahydro-4-hydroxy-2H-pyran-2-one ring is preferred to the cis configuration. The configuration of the trans-tetrahydropyran-2-one moiety of the compounds exemplified infra is composed of the 4R, 6S isomer and the racemate (i.e. 4S, 6R). Positions 4 and 6 of the pyranone ring and 3 to 5 positions of the dihydroxyheptenoic acid form of the compounds present chiral centers (3R, 5S and 3S, 5R). The optical isomers are separated or prepared conventionally. Hence, throughout this specification and the appended claims, reference to the compounds is intended to embrace their stereo and optical isomers as well as racemic mixtures.

The compounds of this invention may be prepared by a variety of synthetic routes using conventional methods. The intermediate furanylacrylaldehyde reactants are obtained from 5-arylfurfurals (commercially available or products of the Meerwein Arylation reaction with furfural) by reaction with a phosphonate ylide according to the Wadsworth-Emmons modification of the Wittig reaction, followed by reduction of the alkoxycarbonyl group to an aldehyde.

The 3-arylfuranylacrylaldehyde reactants are produced by reaction of the appropriately substituted chloroacetophenone with the appropriately substituted, acetylenically unsaturated magnesium bromide derivative followed by (1) dehydrohalogenation of the chlorhydrin to the epoxide, (2) ring enlargement to the acetylenic unsaturation to form the furan ring followed by (3) reaction with 3-dimethylamino acrolein in the presence of phosphoryl trichloride to obtain the 3-arylfuranylacrylaldehyde, thusly:

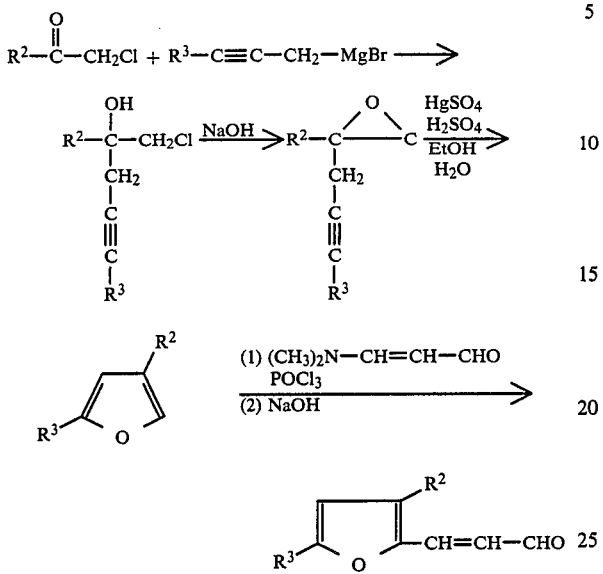

The aldehyde is condensed with the dianion of methyl acetoacetate

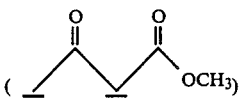

and the product is reduced with a borohydride to afford the methyl ester of the claied dihydroxyheptenoic acid derivatives. Basic hydrolysis, acidification and removal of water yields the claimed lactones. Conversion of the lactones to pharmaceutically acceptable salts is performed in each instance by reaction of the lactone with an equivalent of the desired base.

The following examples illustrate the preparation of representative compounds of this invention.

EXAMPLE 1

(3S,5S,E)-7-[5-Methyl-3-(4-Fluorophenyl)-2-Furanyl]-3,5-Dihydroxy-6-Heptenoic Acid Methyl Ester To a solution of 23.1 g (0.16 mol) of propargylmagnesium bromide (J. Am. Chem. Soc., 83, 1686, 1961) in 50 mL of dry diethyl ether at 25° C. was added 20.0 g (0.115 mol) of 2-chloro-4'-fluoroacetophenone in 150 mL of diethyl ether over a 0.25 hour period. The solution was stirred at 25° C. for 15 hours and then quenched with 50 mL of saturated NH4Cl. The layers were separated and the aqueous phase extracted twice with 100 mL diethyl ether. The combined ether extracts were dried (MgSO4) and the solvent removed at reduced pressure. This residue was dissolved in 250 mL of dry diethyl ether and added to 4.9 g of pulverized NaOH. This mixture was stirred at 24° C. for 3.5 hours and then 0.5 g of NaOH was added. After an additional 2.5 hours, the mixture was poured into 100 mL of H2O and extracted with diethyl ether. The ether layer was separated, dried (MgSO4) and concentrated under reduced pressure. Distillation under reduced pressure (94°-95° C. at 0.65 mmHg) yielded 16 g (79%) of 4,5-epoxy-4-(4'-fluorophenyl)-1-pentyne as an oil, homogeneous by TLC and spectroscopic criteria; $R_f$ 0.75 (1:1 hexanes-diethyl ether): IR (film) 3290, 1600, 1505, 1225 cm$^{-1}$; $^1$HNMR (300 MHz, CDCl3) δ 7.5-7.4 (m, 2H), 7.1-7.05 (m, 2H, 3.02 (AB$_q$, 2H, J$_{AB}$=6.0 Hz, Δv$_{AB}$=119.8 Hz), 2.92 (t, 2H, J=2 Hz), 2.07 (t, 1H, J=2 Hz).

To a solution of 0.46 g (1.5 mmol) of mercuric sulfate in 28 mL of 2N H2SO4 at 0° C. was added 4.0 g (22 mmol) of 4,5-epoxy-4-(4'-fluorophenyl)-1-pentyne in 20 mL of ethanol over a 0.5 hour period. The mixture was warmed to 23° C. for 0.25 hour and refluxed for 0.25 hour. After cooling, the mixture was poured into 50 mL of H2O and extracted three times with hexanes. The organic layer was dried (MgSO4), concentrated under reduced pressure, and the solid sublimated (97°-105° C. at 15 mmHg) to yield 2.2 g (55%) of 2-methyl-4-(4'-fluorophenyl)furan as a solid (m.p. 95°-97° C.), homogeneous by spectroscopic criteria; IR (KBr) 1548, 1495, 1240 cm$^{-1}$; $^1$HNMR (300 MHz, CDCl3) δ 7.55 (s, 1H), 7.43 (m, 2H), 7.07 (t, 2H, J=9 Hz), 6.27 (s, 1H), 2.33 (s, 3H).

A solution of 1.1 mL (11.9 mmol) of phosphorus oxychloride in 15 mL of acetonitrile was allowed to react with 1.2 mL (11.9 mmol) of 3-dimethylaminoacrolein at −23° C. After 0.25 hour at −23° C., 1.4 g (7.9 mmol) of 2-methyl-4-(4'-fluorophenyl)furan in 10 mL of acetonitrile was added dropwise. The reaction mixture was stirred at −23° C. for 0.15 hour then at 24° C. for 2 hours. The reaction was quenched upon treatment with 20 mL of 1M NaOH and extracted three times with CHCl3. The CHCl3 layers were combined, dried (MgSO4) and concentrated under reduced pressure. Column chromatography (3:1 hexanes-diethyl ether) of the residue on silica gel produced 1.76 g (97%) of 3-(5-methyl-3-p-fluorophenyl-furan-2-yl)acrylaldehyde as a solid (m.p. 89°-90° C.), homogeneous by TLC and spectroscopic criteria; $R_f$ 0.58 (1:1 hexanes-diethyl ether); IR (KBr) 1655, 1600, 1205, 1118, 1095 cm$^{-1}$; $^1$HNMR (300 MHz, CDCl3) 9.60 (d, 1H, J=10.5 Hz), 7.41 (m, 2H), 7.27 (d, 1H, J=15 Hz), 7.18 (t, 2H, J=9.0 Hz), 6.64 (dd, 1H, J=10.5 Hz, 15 Hz), 6.32 (s, 1H), 2.42 (s, 3H).

The unsaturated aldehyde (1.0 g, 4.3 mmol) from above was dissolved in 10 mL of dry THF and added dropwise to a solution of 4.9 mmol of the dianion of methyl acetoacetate (J. Am. Chem. Soc., 96, 1082, 1974) in 18 mL of dry THF at −78° C. After 0.4 hour of stirring at −78° C., the solution was warmed to 0° C. and quenched with saturated NH4Cl and poured into 50 mL of H2O. The aqueous phase was extracted twice with chloroform which extracts were combined, dried (MgSO4) and concentrated under reduced pressure. Column chromatography of the residue on silica gel (3:1 hexanes-ethyl acetate) yielded 1.31 g (86%) of the β-keto-ester-5-hydroxy-7-(5-methyl-3-p-fluorophenyl-furan-2-yl)-3-oxo-hept-6-enoic acid methyl ester as an oil, homogeneous by TLC and spectroscopic criteria; $R_f$ 0.57 (1:1 ethyl acetate-hexanes); IR (film) 3450, 1735, 1705, 1545, 1495, 1215 cm$^{-1}$; $^1$HNMR (300 MHz, CDCl3) δ 7.32 (m, 2H), 7.08 (t, 2H, J=9.0 Hz), 6.58 (d, 1H, 15.0 Hz), 6.17 (dd, 1H, J=6.0 Hz, 15.0 Hz), 6.10 (s, 1H), 4.74 (q, 1H, J=7.5 Hz), 3.72 (s, 3H), 3.49 (s, 2H), 2.84 (d, 2H, J=7.5 Hz), 2.31 (s, 3H).

The keto-ester (1.2 g, 3.5 mmol) prepared above was dissolved in 20 mL of 4:1 THF—CH3OH containing 4.16 mL of 1M triethylborane. Four milliliters of air was bubbled in and the mixture allowed to stir at 23° C. for ½ hour. At −90° C., 0.16 g (4.1 mmol) of NaBH4 was added as a solid. After stirring at −90° C. for 1 hour, the reaction was warmed to 0° C. where it was quenched with 7.5 mL of 30% $H_2O_2$ in 22 mL of $H_2O$. Stirring was continued at 23° C. for 0.5 hour when the mixture was poured into 200 mL of ethyl acetate. The organic phase was washed with 30 mL of 1N HCl, 50 mL of $H_2O$ (twice), and saturated brine. The ethyl acetate was dried ($MgSO_4$), concentrated and column chromatographed on silica gel (1:1 ethyl acetate-hexanes) to yield 0.99 g (82%) of the titled compound as an oil, homogeneous by TLC and spectroscopic considerations; $R_f$ 0.35 (1:1 ethyl acetate-hexanes); IR (film) 3400, 1716, 1550, 1492, 1213 cm$^{-1}$;

Elemental Analysis for: $C_{19}H_{21}FO_5$: Calculated: C, 65.51; H, 6.07; Found: C, 65.40; H, 6.06.

Saponification with NaOH affords the sodium salt, which upon acidification yields the free carboxylic acids. Dehydration gives tetrahydro-4-hydroxy-6-[3-p-fluorophenyl-5-methyl-furan-2-ylethenyl]-2H-pyran-2-one.

EXAMPLE 2

(3S,5S,E)-7-[5-Methyl-3-Phenyl-2-Furanyl]-3,5-Dihydroxy-6-Heptenoic Acid Methyl Ester To a solution of 48.1 g (0.34 mol) of propargylmagnesium bromide in 100 mL of dry diethyl ether at 0° C. was added 37.0 g of α-chloroacetophenone in 300 mL of diethyl ether over a 0.75 hour period. The solution was stirred 0.5 hour at 0° C. then at 23° C. for 14 hours. The reaction mixture was quenched with saturated $NH_4Cl$ and the phases separated. The aqueous phase was extracted twice with 100 mL of diethyl ether and the organic layers combined, dried ($MgSO_4$) and concentrated under reduced pressure. The 31 g (68%) of 5-chloro-4-hydroxy-4-phenyl-1-pentyne was distilled (b.p. 103°–105° C. at 0.5 mmHg) and used as is.

The product of the preceding paragraph (31 g) was dissolved in 250 mL of diethyl ether along with 6.8 g of pulverized NaOH and stirred at 23° C. for 2.5 hours. The mixture was poured into 100 mL of $H_2O$ and the layers separated. The aqueous phase was extracted twice with 100 mL of diethyl ether and the organic layers combined, dried ($MgSO_4$) and concentrated under reduced pressure. The 4,5-epoxy-4-phenyl-1-pentyne was distilled (b.p. 70.5°–73.5° C. at 0.5 mmHg) to yield 20.7 g (81%) of liquid which was homogeneous by spectroscopic criteria; IR (film) 3280, 1493, 1443, 1412, 755 cm$^{-1}$; $^1$HNMR (300 MHz, CDCl$_3$) δ 7.55–7.3 (m, 5H), 3.06 (AB$_q$, 2H, J=6.0 Hz, Δν$_{AB}$=122.8 Hz), 2.98 (t, 2H, J=2.0 Hz), 2.09 (t, 1H, J=2.0 Hz).

To a solution of 0.5 g HgSO$_4$ in 30 mL of 2N HgSO$_4$ was added 4.74 g (30 mmol) of 4,5-epoxy-4-phenyl-1-pentyne in 30 mL of absolute ethanol over a 5 minute period. The reaction mixture was refluxed for 0.25 hour and cooled to 23° C. After addition to 150 mL of $H_2O$ the mixture was extracted with hexanes three times. The combined organic layers were dried (MgSO$_4$) and concentrated under reduced pressure. Sublimation (90° C. at 15 mmHg) of the solid gave 3.6 g (76%) of 2-methyl-4-phenylfuran as a solid (m.p. 89°–91° C.) which was homogeneous by spectroscopic considerations; IR (KBr) 1599, 1545, 1440, 742 cm$^{-1}$; $^1$HNMR (300 MHz, CDCl$_3$) δ 7.62 (s, 1H), 7.50 (d, 2H, J=9.0 Hz), 7.38 (t, 2H, J=9.0 Hz), 7.28 (t, 1H, J=9.0 Hz), 6.33 (s, 1H), 2.35 (s, 3H).

A solution of 0.53 mL (5.6 mmol) of phosphorous oxychloride in 5 mL of dry acetonitrile was allowed to react with 0.56 mL (5.6 mmol) of 3-dimethylaminoacrolein at −23° C. After 0.25 hour at −23° C., 0.6 g (3.8 mmol) of 2-methyl-4-phenylfuran in 4 mL of acetonitrile was added dropwise. The reaction mixture was stirred at −23° C. for 0.5 hour, 23° C. for 0.5 hour, then at reflux for 0.5 hour. The reaction mixture was cooled to room temperature, quenched with 20 mL of 1N NaOH and extracted with CHCl$_3$. The organic layer was dried (MgSO$_4$) and concentrated under reduced pressure. Column chromatography of the residue on silica gel (4:1 hexanes-diethyl ether) yielded 1.66 g (78%) of the desired aldehyde as an oil, homogeneous by TLC and spectroscopic criteria; $R_f$ 0.68 (1:1 ethyl acetate-hexanes); IR (film) 1662, 1580, 1125 cm$^{-1}$; $^1$HNMR (300 MHz, CDCl$_3$) δ 9.61 (d, 1H, J=9.0 Hz), 7.44 (m, 5H), 7.34 (d, 1H, J=15.0 Hz), 6.64 (q, 1H, J=9.0 Hz, 15 Hz), 6.36 (s, 1H), 2.46 (s, 3H).

The aldehyde (1.66 g, 7.8 mmol) produced from the procedure above dissolved in 7 mL of dry THF was added dropwise to a solution (8.9 mmol) of the dianion of methyl acetoacetate in 20 mL of THF at −78° C. After 0.5 hour of stirring at −78° C., the solution was warmed to 0° C. for 0.75 hour and quenched with saturated NH$_4$Cl, then poured into 50 mL of H$_2$O. The aqueous solution was extracted twice with CHCl$_3$ which extracts were combined, dried (MgSO$_4$) and concentrated under reduced pressure. Column chromatography of the residue on silica gel (3:1 hexane-ethyl acetate) yielded 1.77 g (70%) of the desired β-keto-ester as an oil, homogeneous by TLC and spectroscopic criteria; $R_f$ 0.45 (1:1 hexane-ethyl acetate); IR (film) 3450, 1735, 1705, 1430, 768 cm$^{-1}$; $^1$HNMR (300 MHz, CDCl$_3$) δ 7.44 (m, 5H), 6.67 (d, 1H, J=15.0 Hz), 6.22 (dd, 1H, J=9.0, 15.0 Hz), 6.19 (s, 1H), 4.78 (q, 1H, 6.0 Hz), 3.78 (s, 3H), 3.56 (s, 2H), 2.88 (d, 2H, J=6.0 Hz), 2.36 (s, 3H).

The keto-ester (1.78 g, 5.4 mmol) prepared above was dissolved in 20 mL of 4:1 THF-methanol containing 8.1 mL of 1N triethylborane. 5 mL of air was bubbled in and the mixture allowed to stir at 23° C. for 0.5 hour. At −85° C., 0.31 g (8.1 mmol) of sodium borohydride was added as a solid. After stirring at −85° C. for 1.5 hour, the mixture was warmed to 0° C. where it was quenched with 11.6 mL of 30% hydrogen peroxide in 33 mL of H$_2$O. Stirring was continued for 0.5 hour at 23° C. when the mixture was poured into 200 mL of ethyl acetate. The organic phase was washed with 50 mL of 1N HCl, 50 mL of H$_2$O (twice) and saturated brine. The ethyl acetate was dried (MgSO$_4$), concentrated and column chromatographed on silica gel (1:1 ethyl acetate-hexanes) to yield 1.28 g (72%) of the titled compound as an oil, homogeneous by TLC and spectroscopic criteria; $R_f$ 19 (1:1 ethyl acetate-hexanes); IR (film) 3420, 1725, 1602, 1438, 760 cm$^{-1}$.

Elemental Analysis for: C$_{19}$H$_{22}$O$_5$: Calculated: C, 69.07; H, 6.71; Found: C, 68.79; H, 6.68.

Saponification with NaOH affords the sodium salt, which upon acification yields the free carboxylic acid. Dehydration gives tetrahydro-4-hydroxy-[3-phenyl-5-methylfuran-2-ylethenyl]-2H-pyran-2-one.

EXAMPLE 3

(3S,5S,E)-7-[3-(4-Fluorophenyl)-2-Furanyl]-3,5-Dihydroxy-6-Heptenoic Acid Methyl Ester To a solution of 0.12 mol of ethynylmagnesium bromide in 300 mL of dry THF at 23° C. was added 15.5 g (90 mmol) of 2-chloro-4'-fluoro-acetophenone as a solid. The mixture stirred at 23° C. for 24 hours when it was quenched with 15 mL of saturated NH4Cl and poured int 250 mL of diethyl ether. The ether layer was separated and washed with H2O, dried (MgSO4) and concentrated. The residue was added to 300 mL of dry diethyl ether and 3.6 g (90 mmol) of pulverized NaOH was added. The reaction mixture was stirred at 23° C. for 3 hours, then the ether was washed twice with 100 mL of H2O and once with saturated brine. The organic layer was dried (MgSO4), concentrated and distillation (b.p. 55°-58° C. at 0.34 mmHg) provided 9.5 g (66%) of 3,4-epoxy-3-(4'-fluorophenyl)-1-butyne as a liquid, homogeneous by spectroscopic criteria; IR (film) 3275, 1595, 1505, 1218 cm$^{-1}$; $^1$HNMR (80 MHz, CDCl3) δ 7.45 (m, 2H), 7.15 (m, 2H), 3.20 (AB$_q$, 2H, J=8.0 Hz, Δν$_{AB}$=39.2 Hz), 2.51 (s, 1H).

To a solution of 0.7 g HgSO4 in 40 mL of 2N H2SO4 was added 5.0 g (31 mmol) of the 3,4-epoxy-3-(4'-fluorophenyl)-1-butyne in 40 mL of absolute ethanol, dropwise. The reaction mixture was refluxed for 0.25 hour and cooled to 23° C. After addition to 50 mL of H2O, the aqueous phase was extracted twice with hexanes. The hexane layers were combined, dried (MgSO4) and concentrated under reduced pressure. Sublimation (90° C. at 0.2 mmHg) of the residue yielded 2.9 g (58%) of the 2-(4'-fluorophenyl)furan as a solid (m.p. 84°-86° C.) homogeneous by spectroscopic criteria; IR (film) 1571, 1505, 1223, 1152, 785 cm$^{-1}$; $^1$HNMR (80 MHz, CDCl3) 7.5-7.0 (m, 6H), 6.65 (m, 1H).

A solution of 0.63 mL (6.7 mmol) of phosphorous oxychloride in 20 mL of dry acetonitrile was allowed to react with 0.68 mL (6.8 mmol) of 3-dimethylaminoacrolein at −23° C. After 0.25 hour at −23° C., 1.0 g (6.16 mmol) of 3-(4'-fluorophenyl)furan in 10 mL of acetonitrile was added dropwise. The reaction mixture was stirred at −23° C. for 0.25 hour, 23° C. for 0.25 hour and then at reflux for 0.25 hour. The mixture was cooled and quenched with 20 mL of 1N NaOH and extracted with CHCl3. The CHCl3 was washed with H2O (twice), saturated brine and then dried (MgSO4) and concentrated under reduced pressure. Column chromatography of the residue on silica gel (3:1 hexanes-diethyl ether) yielded 0.83 g (67%) of the desired aldehyde as a low melting solid, homogeneous by TLC and spectroscopic criteria; R$_f$ 0.62 (1:1 diethyl ether-hexanes); IR (KBr) 1661, 1609, 1505, 822 cm$^{-1}$; $^1$HNMR (300 MHz, CDCl3) δ 9.45 (d, 1H, J=4.3 Hz), 7.50-6.95 (m, 6H), 6.70-6.40 (m, 2H).

The aldehyde (0.8 g, 3.7 mmol) produced from the procedure above, dissolved in 10 mL of dry THF, was added dropwise to a solution containing 4.4 mmol of the dianion of methyl acetoacetate in 40 mL of THF at −78° C. After 0.25 hour at −78° C., the reaction was warmed to 0° C. for 0.25 hour and quenched with saturated NH4Cl. The mixture was then extracted three times with ethyl acetate which was then dried (MgSO4) and concentrated under reduced pressure. Column chromatography of the residue on silica gel (3:1 hexanes-ethyl acetate) yielded 0.94 g (77%) of the desired keto-ester as an oil, homogeneous by TLC and spectroscopic criteria; R$_f$ 0.40 (1:1 ethyl acetate-hexanes); IR (film) 3450, 1740, 1710, 1512, 1220, 835 cm$^{-1}$; $^1$HNMR (300 MHz, CDCl3) δ 7.38 (m, 2H), 7.13 (t, 2H, J=9.0 Hz), 6.63 (d, 1H, J=16.2 Hz), 6.53 (s, 1H), 6.27 (dd, 1H, J=6.9, 16.2 Hz), 4.80 (q, 1H, 6.0 Hz), 3.76 (s, 3H), 3.53 (s, 2H), 2.88 (d, 2H, J=6.0 Hz) 1.8-1.5 (1H, exchangeable).

The keto-ester (0.92 g, 2.8 mmol) prepared above was dissolved in 32 mL of 4:1 THF-methanol containing 4.15 mL of 1N triethylborane. Four milliliters of air was bubbled in and the mixture allowed to stir at 23° C. for 0.5 hour. At −85° C., 0.16 g (4.1 mmol) of sodium borohydride was added as a solid. After stirring at −90° C. for 1.5 hour, the reaction was warmed to 23° C. where it was quenched with 7 mL of 30% H2O2 in 33 mL of H2O. Stirring was continued for 0.5 hour at 23° C., and the solution was then poured into 200 mL of ethyl acetate. The organic phase was washed with 50 mL of 1N HCl, 50 mL of H2O (twice) and saturated brine. The ethyl acetate was dried (MgSO4), concentrated and column chromatography of the residue on silica gel (1:1 ethyl acetate-hexane) yielded 0.625 g (51%) of the titled compound as an oil, homogeneous by TLC and spectroscopic criteria; R$_f$ 0.28 (1:1 ethyl acetate-hexanes); IR (film) 3430, 1729, 1512, 1220, 835 cm$^{-1}$.

Elementary Analysis for: C$_{18}$H$_{19}$FO$_5$ Calculated: C, 64.66; H, 5.73 Found: C, 64.32; H, 5.66

Saponification with NaOH affords the sodium salt, which upon acidification yields the free carboxylic acid. Dehydration gives tetrahydro-4-hydroxy-6-(3-p-fluorophenylfuran-2-ylethenyl)-2H-pyran-2-one.

EXAMPLE 4

(3S,5S,E)-3,5-Dihydroxy-7-[5-[4-(Trifluoromethyl)-2-Nitrophenyl]-2-Furanyl]-6-Heptenoic Acid Methyl Ester To a solution of 0.23 g (5.55 mmol) of hexanes washed 60% sodium hydride in 20 mL of dry THF was added, at −23° C., 1.05 mL (5.25 mmol) of triethylphosphonoacetate. After 0.75 hour at −23° C., 1.5 g (5.25 mmol) of 5-(2-nitro-4-(trifluoromethyl)phenyl)furaldehyde in 10 mL of THF was added dropwise. The reaction mixture stirred at −23° C. for 0.5 hour then at 23° C. for 1 hour. The reaction was quenched with saturated NH4Cl and poured into 50 mL of H2O. Extraction with ethyl acetate (3 times), conbination of the organic layers, drying (MgSO4) and concentration under reduced pressure gave an oily residue. Column chromatography of the residue on silica gel (4:1 hexanes-ethyl acetate) yielded 1.54 g (83%) of the unsaturated ester 5-(2-nitro-4-trifluoromethylphenyl)-furan-2-ylacrylic acid ethyl ester as an oil, homogeneous by TLC and spectroscopic criteria; R$_f$ 0.75 (1:1 ethyl acetate-hexanes); IR (film) 1690, 1610, 1507, 1140 cm$^{-1}$; $^1$HNMR (300 MHz, CDCl3) δ 7.96 (m, 2H), 7.88 (d, 1H, J=9.0 Hz), 7.46 (d, 1H, J=16.8 Hz), 6.89 (d, 1H, J=1.2 Hz), 6.74 (d, 1H, J=1.2 Hz), 6.42 (d, 1H, J=16.8 Hz), 4.3 (q, 2H, J=7.8 Hz), 1.35 (t, 3H, J=7.8 Hz).

The ester (1.54 g, 4.3 mmol) produced above was dissolved in 25 mL of dry THF and cooled to −78° C. 6.35 Milliliters (9.5 mmol) of diisobutylaluminum hydride was added dropwise. After stirring at −78° C. for 0.75 hour the flask was warmed to 0° C. where the mixture stirred for 0.75 hour. The reaction mixture was quenched with saturated Na2SO4 and added to 100 mL of 1N HCl. Extraction with ethyl acetate (3×100 mL) and combination of the organic layers gave an oily residue after drying (MgSO4) and concentration under reduced pressure. The residue was added to 70 mL of CHCl3 and 7.5 g (86 mmol) of activated MnO2 at 23° C. After stirring for 10 hours the reaction mixture was filtered through celite, which was washed with additional CHCl3. The CHCl3 was concentrated and the residue was chromatographed on silica gel (3:1 hexane-ethyl acetate) to yield 0.72 g (54%) of the desired aldehyde as an oil, homogeneous by TLC and spectroscopic criteria; $R_f$ 0.59 (1:1 hexanes-ethyl acetate); IR (film) 1678, 1627, 1538, 1326 cm$^{-1}$; $^1$HNMR (300 MHz, CDCl$_3$) δ 9.72 (d, 1H, J=8.4 Hz), 8.03–7.9 (m, 3H), 6.94 (m, 3H), 6.68 (dd, 1H, J=8.4 Hz, 16.2 Hz).

The aldehyde (0.72 g, 2.3 mmol) produced from the above procedure, was dissolved in 8 mL of dry THF and added to a mixture of 2.5 mmol of the dianion of methyl acetoacetate in 20 mL of THF at −78° C. The reaction mixture was stirred at −78° C. for 0.25 hour and then warmed to 0° C. for 0.75 hour. The mixture was quenched with 10 mL of saturated NH$_4$Cl and extracted three times with CHCl$_3$. The combined extracts were dried (MgSO$_4$) and concentrated under reduced pressure to give an oil which was chromatographed on silica gel (1:1 ethyl acetate-hexane) to yield 0.36 g (37%) of the desired keto-ester as an oil, homogeneous by TLC and spectroscopic criteria; $R_f$ 0.31 (1:1 ethyl acetate-hexane); IR (film) 3450, 1739, 1710, 1532, 1320 cm$^{-1}$; $^1$HNMR (300 MHz, CDCl$_3$) δ 7.98–7.80 (m, 3H), 6.84 (d, 1H, J=4.2 Hz), 6.56 (d, 1H, J=15.6 Hz), 6.42 (d, 1H, J=4.2 Hz), 6.28 (dd, 1H, J=6 Hz, 15.6 Hz), 4.85 (m, 1H), 3.78 (s, 3H), 3.55 (s, 2H), 2.90 (m, 2H).

The keto-ester (0.34 g, 0.8 mmol) from above was dissolved in 10 mL of 4:1 THF-methanol containing 1.2 mL of 1N triethylborane. Three milliliters of air was bubbled in and the mixture stirred at 23° C. for 0.5 hour. At −80° C., 0.45 (1.2 mmol) of sodium borohydride was added as a solid. After stirring at −80° C. for 1 hour the reaction was warmed to 0° C. and quenched with 1.4 mL of 30% H$_2$O$_2$ in 4.5 mL of H$_2$O. Stirring was continued for 0.5 hour at 23° C., then the mixture was poured into 200 mL of ethyl acetate. The organic layer was washed with 30 mL of 1N HCl, 30 mL of H$_2$O (twice) and with saturated brine. The ethyl acetate was dried (MgSO$_4$) and concentrated under reduced pressure. The residue was column chromatographed on silica gel (1:1 ethyl acetate-hexanes) to yield 0.23 g (69%) of the titled compound as an oil, homogeneous by TLC and spectroscopic criteria; $R_f$ 0.21 (1:1 ethyl acetate-hexanes); IR (film) 3400, 1728, 1538, 1322 cm$^{-1}$.

Elemental Analysis for: C$_{19}$H$_{18}$F$_3$NO$_7$: Calculated: C, 53.15; H, 4.22; N, 3.26; Found: C, 53.49; H, 4.12; N, 3.01.

Saponification with NaOH affords the sodium salt, which upon acidification yields the free carboxylic acid. Dehydration gives tetrahydro 4-hydroxy-6-[5-(2-nitro-4-trifluoromethylphenyl)-furan-2-yl ethenyl]-2H-pyran-2-one.

The HMG—CoA reductase inhibitory properties of representative compounds of this invention were established by subjecting the compounds to the following standard experimental test procedure adapted from Rodwell et al., Adv. Lipid Res. 14 1, 1976; Endo et al., FEBS Letters 72 323, 1976; and Tanzawa et al., Biochemia et Biophysica Acta 488 97, 1977.

Rat livers obtained from rats fed on a diet containing 3% cholestyramine and maintained on a reverse lighting regimen for three weeks are homogenized and the microsomal fraction is isolated by differential ultracentrifugation to obtain HMG—CoA reductase enzyme. To a preincubated (five minutes at 37° C.) solution of the compound being tested (as the dihydroxy sodium carboxylate in amounts from 10$^{-3}$ to 10$^{-6}$M) in TEDKS$_{100}$pH (Tris ®40 mM; EDTA 1 mM; dithiothreitol 5 mM; KCl 70 mM; sucrose 100 mM), 7.5 buffer or DMSO dissolved in an assay medium containing 20 μl of 2.5M KCl; 20 μl NADPH (reduced nicotinamide adenine dinucleotide phosphate) (7.5 mM); and 40 μl of labeled (RS) HMG—CoA (3—$^{14}$C; 0.4 Ci; 200 μM) is added 10 μl of preincubated (five minutes at 37° C.) microsomal fraction to obtain a total volume of 125 μl. After a twenty minute incubation period at 37° C., reaction of the enzyme is terminated by addition of 10 μl of 70% HClO$_4$. The assay tubes are then centrifuged for two minutes in a Beckman microfuge II.

To 100 μl of the supernatant liquid is added 10 μl of non-radioactive mevalonic acid lactone (0.25M in 8 mM H$_2$SO$_4$). An aliquot of the sample is eluted with 8 mM H$_2$SO$_4$ through Bio Rad Aminex HPX-87H (HPLC; Hewlett-Packard Model 1084B) at a flow rate of 1 mL/minute. The effluent is fractionated, Hydrofluor ® is added and radioactivity of the [$^{14}$C] mevalonolactone produced by reduction of [$^{14}$C] HMG—CoA determined with a scintillation counter.

The percent inhibition of HMG—CoA reductase activity is obtained by comparison with a control assay devoid of the test compound. The inhibitory concentration (IC$_{50}$) is calculated for the various test compounds.

The results of these experiments were as follow:

| Compound of Example No. | Inhibition of HMG—CoA Reductase (IC$_{50}$, μM) |
|---|---|
| 1 | 62.0 |
| 2 | 99.0 |
| 3 | 56.0 |
| 4 | 100 |

Thus, the compounds of this invention are established as potent inhibitors of HMG—CoA reductase, which categorizes them as anti-hypercholesterolemic agents useful in the treatment of disease states in which reduced levels of cholesterol are desired, such as atherosclerosis, familial hypercholesterolaemia, hyperlipaemia, and the like.

Administration of the compounds of this invention, in suitable dosage form, may be by the oral or parenteral routes, in single or plural doses as needed to reduce cholesterol blood plasa levels. The specific dosage regimen for a given patient will depend upon age, size, pathological state, severity of dysfunction, etc. and may be individualized by the attending physician by following blood lipid levels. Sustained release formulations for oral administration by tablet or capsule are especially suitable for administration of the HMG—CoA reductase inhibitors of this invention.

What is claimed is:

1. A compound of the formula:

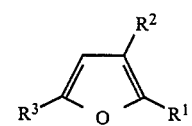

in which

R$^1$ is —CH=CHCHCH$_2$CHCH$_2$CO$_2$M or
   OH   OH

-continued

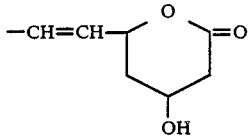

where M is hydrogen or alkyl of 1 to 4 carbon atoms;
one of $R^2$ and $R^3$ is phenyl or substituted phenyl containing 1 or 2 substituents which are, independently, alkyl of 1 to 8 carbon atoms, alkoxy of 1 to 8 carbon atoms, halogen, trifluoromethyl, nitro, amino, cyano or carboxyl; and the other of $R^2$ and $R^3$ is hydrogen, alkyl of 1 to 8 carbon atoms; or a halogen;
or a pharmaceutically acceptable salt thereof.

2. A compound of claim 1 of the formula:

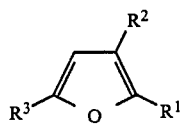

in which $R^1$ is $-CH=CHCHCH_2CHCH_2CO_2M$ or
$\phantom{R^1 is -CH=CHC}\overset{|}{OH}\phantom{CH_2}\overset{|}{OH}$

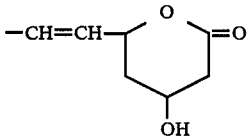

where M is hydrogen or alkyl of 1 to 4 carbon atoms; one of $R^2$ and $R^3$ is phenyl or substituted phenyl containing 1 or 2 substituents which are, independently, halogen, nitro or trifluoromethyl, and the other of $R^2$ and $R^3$ is hydrogen or alkyl of 1 to 4 carbon atoms; or a pharmaceutically acceptable salt thereof.

3. A compound of claim 1 which is (3S,5S,E)-7-[5-methyl-3-(4-fluorophenyl)-2-furanyl]-3,5-dihydroxy-6-heptenoic acid, its alkyl esters in which the alkyl group contains 1 to 4 carbon atoms, or a pharmaceutically acceptable salt thereof.

4. A compound of claim 1 which is (3S,5S,E)-7-[5-methyl-3-phenyl-2-furanyl]-3,5-dihydroxy-6-heptenoic acid, its alkyl esters in which the alkyl group contains 1 to 4 carbon atoms, or a pharmaceutically acceptable salt thereof.

5. A compound of claim 1 which is (3S,5S,E)-7-[3-(4-fluorophenyl)-2-furanyl]-3,5-dihydroxy-6-heptenoic acid, its alkyl esters in which the alkyl group contains 1 to 4 carbon atoms, or a pharmaceutically acceptable salt thereof.

6. A compound of claim 1 which is (3S,5S,E)-3,5-dihydroxy-7-[5-[4-(trifluoromethyl)-2-nitrophenyl]-2-furanyl]-6-heptenoic acid, its alkyl esters in which the alkyl group contains 1 to 4 carbon atoms, or a pharmaceutically acceptable salt thereof.

7. The compound of claim 1 which is tetrahydro-4-hydroxy-6-[3-p-fluorophenyl-5-methyl-furan-2-ylethenyl]-2H-pyran-2-one.

8. The compound of claim 1 which is tetrahydro-4-hydroxy-[3-phenyl-5-methyl-furan-2-ylethenyl]-2H-pyran-2-one.

9. The compound of claim 1 which is tetrahydro-4-hydroxy-6-(3-p-fluorophenyl-furan-2-ylethenyl)-2H-pyran-2-one.

10. The compound of claim 1 which is tetrahydro-4-hydroxy-6-[5-(2-nitro-4-trifluoromethylphenyl)-furan-2-ylethenyl]-2H-pyran-2-one.

* * * * *